(12) United States Patent
Hatano et al.

(10) Patent No.: US 11,337,591 B2
(45) Date of Patent: May 24, 2022

(54) ENDOSCOPE

(71) Applicant: OLYMPUS CORPORATION, Tokyo (JP)

(72) Inventors: Keisuke Hatano, Fuchu (JP); Yudai Harada, Neyagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 198 days.

(21) Appl. No.: 16/798,998

(22) Filed: Feb. 24, 2020

(65) Prior Publication Data

US 2020/0205642 A1 Jul. 2, 2020

Related U.S. Application Data

(63) Continuation of application No. PCT/JP2018/032644, filed on Sep. 3, 2018.

(30) Foreign Application Priority Data

Oct. 2, 2017 (JP) .............................. JP2017-192782

(51) Int. Cl.
*A61B 1/00* (2006.01)
*A61B 1/005* (2006.01)
(Continued)

(52) U.S. Cl.
CPC .......... *A61B 1/0057* (2013.01); *A61B 1/0053* (2013.01); *A61B 1/00082* (2013.01);
(Continued)

(58) Field of Classification Search
None
See application file for complete search history.

(56) References Cited

U.S. PATENT DOCUMENTS 4,762,118 A * 8/1988 Lia ...................... A61B 1/0055
138/120
4,841,950 A 6/1989 Fukuda
(Continued)

FOREIGN PATENT DOCUMENTS

EP 2359741 A1 8/2011
JP H01-104237 A 4/1989
(Continued)

OTHER PUBLICATIONS

International Search Report dated Nov. 27, 2018 issued in PCT/JP2018/032644.

*Primary Examiner* — Timothy J Neal
(74) *Attorney, Agent, or Firm* — Scully, Scott, Murphy & Presser, P.C.

(57) ABSTRACT

An endoscope includes a bending operation member provided at an operation portion and configured to bend a bending portion of an insertion portion, a plurality of bending operation wires configured to be pulled or relaxed by the bending operation member, a plurality of tubular members provided inside the operation portion, into which the plurality of bending operation wires are inserted respectively, and disposed in a deflected state so as to avoid an internal component provided inside the operation portion, and a tubular member fixing member provided inside the operation portion and enabled to optimally adjust end portions of the plurality of tubular members at different positions along a longitudinal axis of the operation portion in a direction orthogonal to the longitudinal axis.

10 Claims, 10 Drawing Sheets

(51) Int. Cl.
  *A61B 1/018* (2006.01)
  *A61B 1/04* (2006.01)
  *G02B 23/24* (2006.01)

(52) U.S. Cl.
  CPC ............... *A61B 1/018* (2013.01); *A61B 1/04* (2013.01); *G02B 23/2484* (2013.01)

(56) References Cited

U.S. PATENT DOCUMENTS

| | | | |
|---|---|---|---|
| 4,905,666 | A | 3/1990 | Fukuda |
| 8,137,308 | B2 * | 3/2012 | Schultz ............. A61M 25/0147 604/95.04 |
| 2007/0232858 | A1 * | 10/2007 | Macnamara ......... A61B 1/0052 600/149 |
| 2009/0143647 | A1 * | 6/2009 | Banju .................. A61B 1/0057 600/149 |
| 2011/0237891 | A1 | 9/2011 | Sato et al. |

FOREIGN PATENT DOCUMENTS

| | | |
|---|---|---|
| JP | H04-8339 A | 1/1992 |
| JP | 4755732 B2 | 6/2011 |
| JP | 2014-073219 A | 4/2014 |
| JP | 6301014 B2 | 3/2018 |
| WO | WO 2011/052372 A1 | 5/2011 |
| WO | WO 2017/163460 A1 | 9/2017 |

\* cited by examiner

ENDOSCOPE

CROSS REFERENCE TO RELATED APPLICATION

This application is a continuation application of PCT/JP2018/032644 filed on Sep. 3, 2018 and claims benefit of Japanese Application No. 2017-192782 filed in Japan on Oct. 2, 2017, the entire contents of which are incorporated herein by this reference.

BACKGROUND OF INVENTION

1. Field of the Invention

The present invention relates to an endoscope configured to bend a bending portion using a plurality of bending operation wires.

2. Description of the Related Art

Conventionally, endoscopes that can be inserted into a subject or object to observe locations inside the subject or object, interiors of which are difficult to observe such as interiors of a living body or a structure, have been widely used, for example, in a medical field or an industrial field.

An insertion portion of such an endoscope is provided with a bending portion configured to improve insertability and observability in the subject or object. The bending portion is subjected to a bending operation by a bending operation portion provided on a top side of the operation portion.

As disclosed, for example, in International Publication No. WO2011/052372, an endoscope configured to bend a bending portion by pulling or relaxing a plurality of bending operation wires through rotating operation of a lever-type bending operation lever as a bending operation portion is known.

SUMMARY OF THE INVENTION

An endoscope according to an aspect of the present invention includes a bending operation member provided at an operation portion and configured to bend a bending portion of an insertion portion, a plurality of bending operation wires configured to be pulled or relaxed by the bending operation member, a plurality of tubular members provided inside the operation portion, into which the plurality of bending operation wires are inserted respectively, and disposed in a deflected state so as to avoid an internal component provided inside the operation portion, and a tubular member fixing member provided inside the operation portion and enabled to freely adjust end portions of the plurality of tubular members to different positions along a longitudinal axis of the operation portion in a direction orthogonal to the longitudinal axis of the operation portion, in which the tubular member fixing member includes a fixing member rotatably provided in the operation portion and configured to fix the plurality of tubular members at rotating positions to adjust deflections of the plurality of tubular members.

DETAILED DESCRIPTION OF THE PREFERRED EMBODIMENT

Hereinafter, a preferred embodiment of the present invention will be described with reference to the accompanying drawings.

Note that the drawings used for the following description are shown on scales differing from one component to another so that the respective components are shown in sizes that are recognizable in the drawings. However, the present invention is not limited only to quantities of the components, shapes of the components, size ratios among the components and relative positional relationships among the components described in the respective drawings. In the following description, there are cases where an up-down direction as viewed toward the plane of the sheet is described as upper and lower parts of the components.

Figure 1:
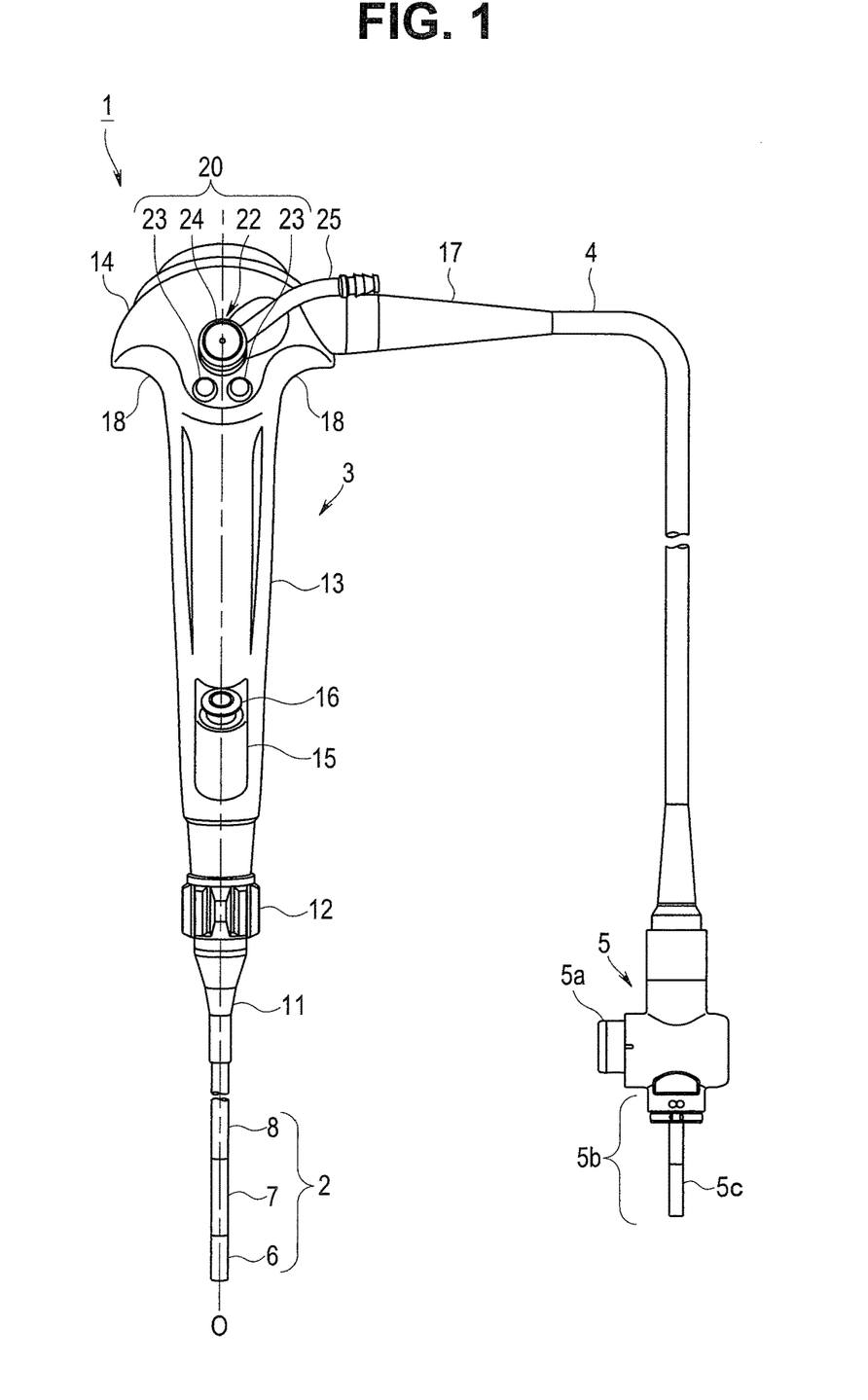
FIG. 1 is a front view illustrating a configuration of an endoscope.
Figure 2:
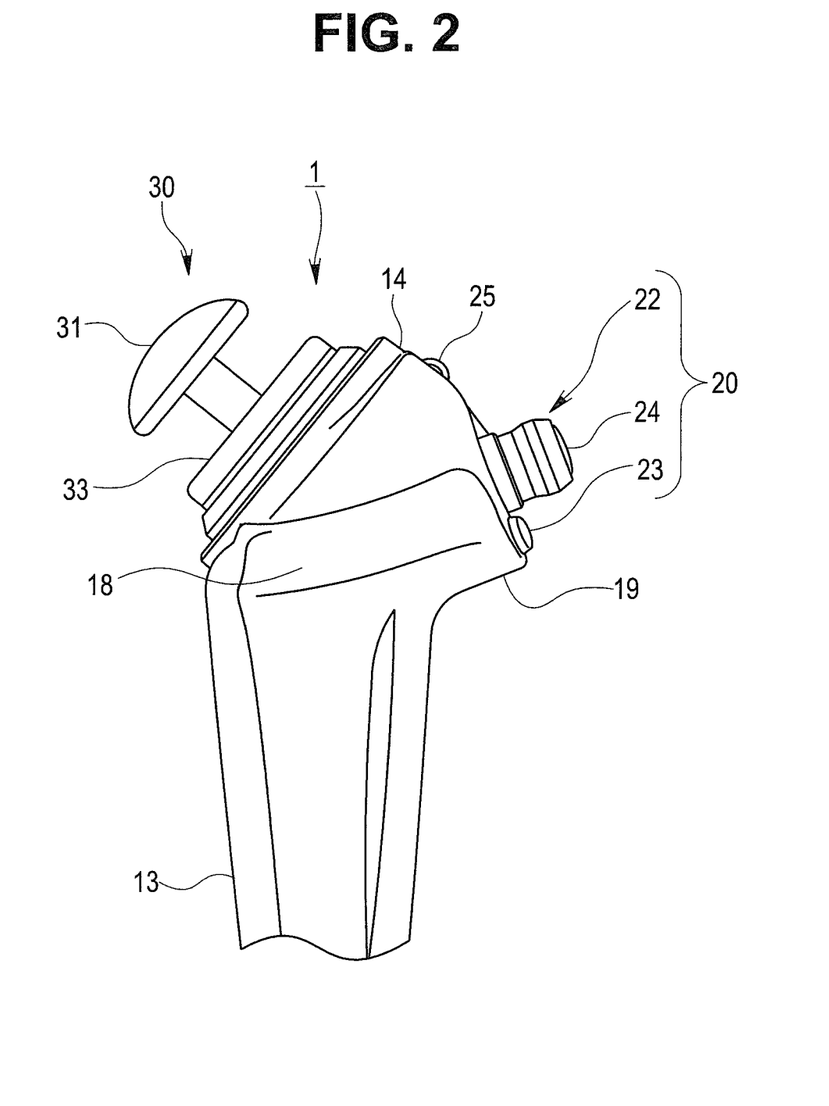
FIG. 2 is a side view illustrating a top portion of an operation portion.
Figure 3:
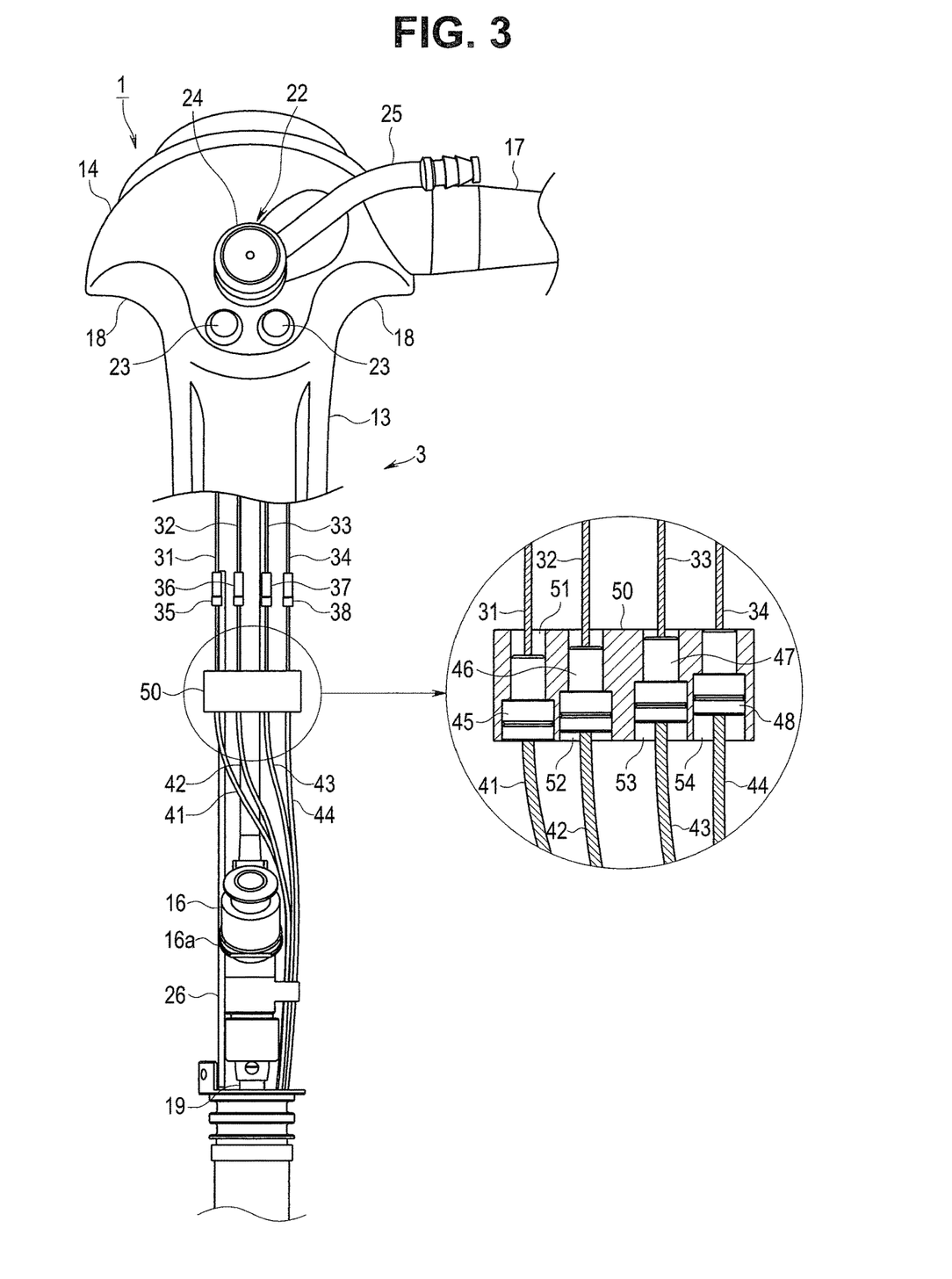
FIG. 3 is a diagram illustrating an internal configuration of the operation portion.
Figure 4:
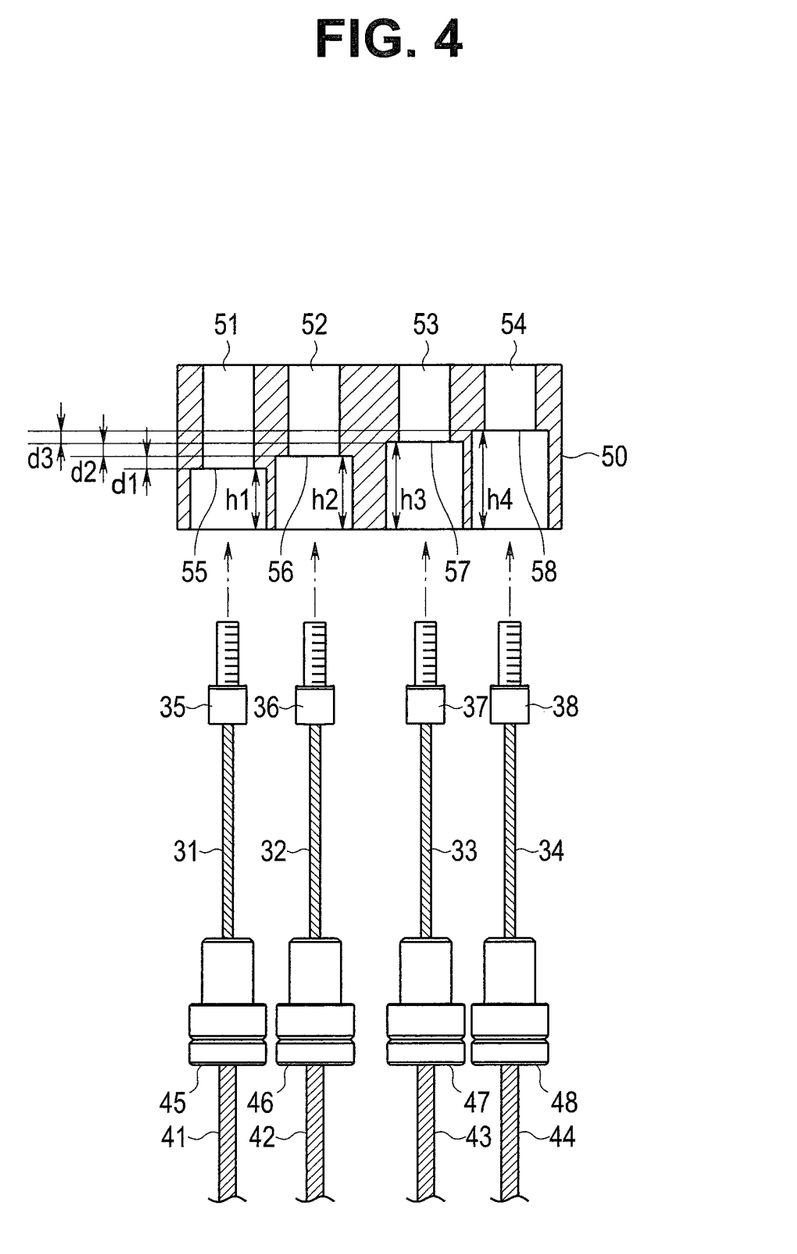
FIG. 4 is a cross-sectional view illustrating a configuration of a coil receiver to which coil tubes are locked.

FIG. 1 is a front view illustrating a configuration of an endoscope, FIG. 2 is a side view illustrating a top part of an operation portion, FIG. 3 is a diagram illustrating an internal configuration of the operation portion and FIG. 4 is a cross-sectional view illustrating a configuration of a coil receiver to which coil tubes are locked.

First, the endoscope of the present embodiment will be described hereinafter.

An endoscope 1 of the present embodiment shown in FIG. 1 and FIG. 2 is an electronic endoscope constructed of an elongated tubular insertion portion 2, an operation portion 3 connected at a proximal end of the insertion portion 2, a universal cord 4, which is an endoscope cable extending from the operation portion 3, and an endoscope connector 5 disposed at a distal end of the universal cord 4.

The insertion portion 2 of the endoscope 1 is constructed of a flexible tubular member in which a distal end portion 6, a bending portion 7, and a flexible tube portion 8 are connected in that order from a distal end side.

An image pickup unit incorporating an objective optical system, an image sensor such as a CCD, CMOS, an illumination optical system configured to radiate illumination light transmitted by a light guide bundle, and a channel pipe configured to connect and hold a treatment instrument channel or the like are disposed in the distal end portion 6 of the insertion portion 2 or the operation portion 3, which are not shown here.

The bending portion 7 of the insertion portion 2 is configured to be able to actively bend in all directions around an insertion axis O including up-down and left-right directions (UP-DOWN/RIGHT-LEFT) in response to operation input by a user, who is an operator of the operation portion 3.

The flexible tube portion 8 of the insertion portion 2 is composed of a flexible tubular member, which is passively bendable. An image pickup cable, the light guide bundle, the treatment instrument insertion channel and an air/water feeding tube (none of which is shown) are inserted into the flexible tube portion 8.

The operation portion 3 of the endoscope 1 is constructed of a bending prevention portion 11 connected to the flexible tube portion 8 with a proximal end of the flexible tube portion 8 being covered, an insertion portion rotation dial 12 provided on a proximal end side of the bending prevention portion 11 configured to freely adjust a rotation position of the insertion portion 2 around the insertion axis O, a grasping portion 13 connected to a proximal end side of the insertion portion rotation dial 12 that can be grasped by the hand of the user, and an operation portion body 14 connected to a proximal end side of the grasping portion 13.

Note that in the present embodiment, the direction or the like around the insertion axis O as a longitudinal axis of the operation portion 3 is defined using a state in which the user grasps the grasping portion 13 as a reference, and more specifically, the front-back and left-right directions (front, rear and left-right sides or the like) are defined for the operation portion 3 using the user who grasps the grasping portion 13 as a reference.

The grasping portion 13 is formed bisymmetrically with respect to the insertion axis O so as to be grasped by the user either by the left or right hand.

A treatment instrument insertion portion 15 is provided in front of the grasping portion 13 on a distal end side. The treatment instrument insertion portion 15 is provided with a treatment instrument insertion port 16 through which various treatment instruments (not shown) are inserted.

The treatment instrument insertion channel communicates with the treatment instrument insertion port 16 via a branch member (neither of which is shown) in the operation portion 3. For example, a disposable forceps plug, which is a lid member (not shown) to close the treatment instrument insertion port 16, is detachably attached to the treatment instrument insertion portion 15.

The operation portion body 14 is constructed of a hollow member that has a substantially partially spherical shape bulging mainly leftward/rightward and forward on the proximal end side of the grasping portion 13. Operation buttons 20 configured to execute a suction function and various optical system functions or the like for the endoscope 1 are disposed on the front side of the operation portion body 14.

These operation buttons 20 are constructed of, for example, a disposable suction valve 22 detachably attached to the operation portion body 14 and two button switches 23 capable of being electively assigned to an arbitrary function, for example, a release button from among the various functions relating to the endoscope 1.

Note that the suction valve 22 is constructed of a suction button 24 as an operation input member and a tube connection portion 25 to which a suction tube extending from an endoscope aspirator which is an external device (not shown) is connected.

The universal cord 4 extends from one side portion (e.g., left side portion) of the operation portion body 14 via the cable bending prevention portion 17.

A bending operation lever portion 30 as a bending operation member configured to bend the bending portion 7 is disposed on a rear side of the operation portion body 14 as shown in FIG. 2.

Here, as shown in FIG. 1, the left-right shape of the operation portion body 14 is a bulging shape, which is bisymmetrical with respect to the insertion axis O, and guiding concave portions 18 configured to guide the forefinger of the user grasping the grasping portion 13 to the operation buttons 20 are formed on the left and right sides on the distal end side of the operation portion body 14 respectively.

The universal cord 4 is a composite cable extending from the distal end portion 6 side through the insertion portion 2 to the operation portion 3 configured to allow insertion of various signal lines including the image pickup cable extending from the operation portion 3, the light guide bundle and the air/water feeding tube into which an air/water feeding fluid flows (neither of which is shown) therein.

The endoscope connector 5 provided at an end portion of the universal cord 4 includes an electric connector portion 5a provided on a side face portion and a light source connector portion 5b connected to a light source apparatus, which is an external device (not shown).

Note that a connector of an electric cable extended from a video processor, which is an external device (not shown) is detachably connected to the electric connector portion 5a. A light guide connector portion 5c housing the light guide bundle is disposed in the light source connector portion 5b.

As shown in FIG. 3, a frame 26 or the like is provided in the operation portion 3 and a conduit branch portion 16a or the like connected the treatment instrument insertion port 16, which becomes an internal component, is fixed to the frame 26. The treatment instrument insertion port 16 communicates with the treatment instrument channel 19 via the conduit branch portion 16a.

In the operation portion 3, four, first to fourth bending operation wires 31, 32, 33 and 34 are provided, which are configured to actively bend the bending portion 7 in four directions, up, down, left and right by being pulled and relaxed according to tilting operation of the bending operation lever portion 30, the four wires having substantially the same length.

Turn buckles 35, 36, 37 and 38 for adjusting lengths are interposed at intermediate portions of the four, first to fourth bending operation wires respectively, and the four bending operation wires are inserted into four, first to fourth coil tubes 41, 42, 43 and 44 as tubular members densely wound with a metal elemental wire or the like such that the respective bending operation wires can freely move back and forth.

These four, first to fourth coil tubes 41, 42, 43 and 44 have substantially the same length, one end of each of the coil tubes being fixedly held to a coil receiver 50, which is a tubular member fixing member in the operation portion 3 and the coil tubes being inserted in a deflected state so as to avoid the conduit branch portion 16a or the like connected to the treatment instrument insertion port 16.

First to fourth connection terminals 45, 46, 47 and 48 as cylindrical locked members having an outward flange are disposed at one end portions, which become respective distal end sides (insertion portion 2 sides) of the four, first to fourth coil tubes 41, 42, 43 and 44.

The coil receiver 50 as the tubular member fixing member is a block body fixed to the frame 26 and formed of a rectangular metal, rigid resin or the like.

As shown in FIG. 4, the coil receiver 50 includes first to fourth locking portions 51, 52, 53 and 54 as four locking members, as through holes here, in which first to fourth inward flanges 55, 56, 57 and 58 configured to respectively lock and fix the first to fourth connection terminals 45, 46, 47 and 48 of the first to fourth coil tubes 41, 42, 43 and 44 are formed.

Note that the first to fourth locking portions 51, 52, 53 and 54 are not limited to through holes, but need only to have the ability to lock the first to fourth connection terminals 45, 46, 47 and 48, and may be groove portions or the like.

In the first to fourth locking portions 51, 52, 53 and 54 formed in the coil receiver 50 of the present embodiment, the first to fourth inward flanges 55, 56, 57 and 58 each have different heights (depths).

More specifically, the first inward flange 55 of the first locking portion 51 is formed to a length h1 where a depth from the top surface side of the coil receiver 50 is smallest, and the second inward flange 56 of the second locking portion 52 is formed to a length h2 where a depth from the top surface side of the coil receiver 50 is second smallest.

The third inward flange 57 of the third locking portion 53 is formed to a length h3 where a depth from the top surface side of the coil receiver 50 is third smallest, and the inward flange 58 of the locking portion 54 is formed to a length h4 where a depth from the top surface side of the coil receiver 50 is largest.

Furthermore, a difference between the length h1 and the length h2 is set to a length d1, a difference between the length h2 and the length h3 is set to a length d2 and a difference between the length h3 and the length h4 is set to a length d3.

In other words, a height (depth) difference between the first inward flange 55 of the first locking portion 51 and the fourth inward flange 58 of the fourth locking portion 54 is largest, and the difference corresponds to a total (d1+d2+d3) of the lengths d1, d2 and d3.

The depths of the first to fourth inward flanges 55, 56, 57 and 58 formed in the first to fourth locking portions 51, 52, 53 and 54 are set to suppress differences in the amount of deflection when the first to fourth coil tubes 41, 42, 43 and 44 are disposed so as to avoid the conduit branch portion 16a or the like of the internal component, which becomes an obstacle.

In other words, the first coil tube 41 is locked to the coil receiver 50 at a farthest position to avoid the conduit branch portion 16a or the like. The second coil tube 42 and the third coil tube 43 are locked to the coil receiver 50 at second and third farthest positions respectively, and the fourth coil tube 44 is locked to the coil receiver 50 at a nearest position.

Therefore, the first inward flange 55 of the first locking portion 51 that locks the first connection terminal 45 of the first coil tube 41 is made shallowest, the second inward flange 56 of the second locking portion 52 that locks the second connection terminal 46 of the second coil tube 42 and the third inward flange 57 of the third locking portion 53 that locks the third connection terminal 47 of the third coil tube 43 are made second and third shallowest, respectively and the fourth inward flange 58 that locks the fourth connection terminal 48 is made deepest.

In this way, in the present embodiment, the coil receiver 50 can optimally adjust the positions at which the end portions of the first to fourth coil tubes 41, 42, 43 and 44 disposed with different amounts of deflection are locked and fixed.

In other words, since the first to fourth coil tubes 41, 42, 43 and 44 each have substantially the same length and the first to fourth bending operation wires 31, 32, 33 and 34 also have substantially the same length, if the locking positions at the coil receiver 50 are the same position in a direction orthogonal to the insertion axis O, the fourth coil tube 44 locked to the coil receiver 50 at the nearest position has a largest amount of deflection and the amount of deflection decreases toward the first coil tube 41 locked to the coil receiver 50 at the farthest position. Thus, when the amounts of deflection of the first to fourth coil tubes 41, 42, 43 and 44 differ considerably, the tension of the first to fourth bending operation wires 31, 32, 33 and 34 varies.

Therefore, in the present embodiment, the coil receiver 50 optimally adjusts the respective amounts of deflection of the first to fourth coil tubes 41, 42, 43 and 44 and suppresses variations in the tension of the first to fourth bending operation wires 31, 32, 33 and 34.

In other words, the coil receiver 50 locks the distal ends of the first to fourth coil tubes 41, 42, 43 and 44 so as to be juxtaposed at different positions along the longitudinal axis in the direction orthogonal to the insertion axis O or the longitudinal axis of the operation portion 3 here, and thereby optimally adjusts the respective amounts of deflection of the first to fourth coil tubes 41, 42, 43 and 44.

As a result, the amounts of traction forces of the first to fourth bending operation wires 31, 32, 33 and 34 for actively bending the bending portion 7 in accordance with the amount of operation (amount of tilting) of the bending operation lever portion 30, which is a bending operation member, become equal, making it possible to prevent variations in the bending angle of the bending portion 7 in accordance with the amount of operation (amount of tilting) of the bending operation lever portion 30 from occurring.

As described above, the endoscope 1 of the present embodiment can suppress variations in the amounts of traction forces of the first to fourth bending operation wires 31, 32, 33 and 34 that bend the bending portion 7 of the insertion portion 2 and make the bending angle of the bending portion 7 substantially uniform in accordance with the amount of operation of the bending operation lever portion 30.

(First Modification)

Figure 5:
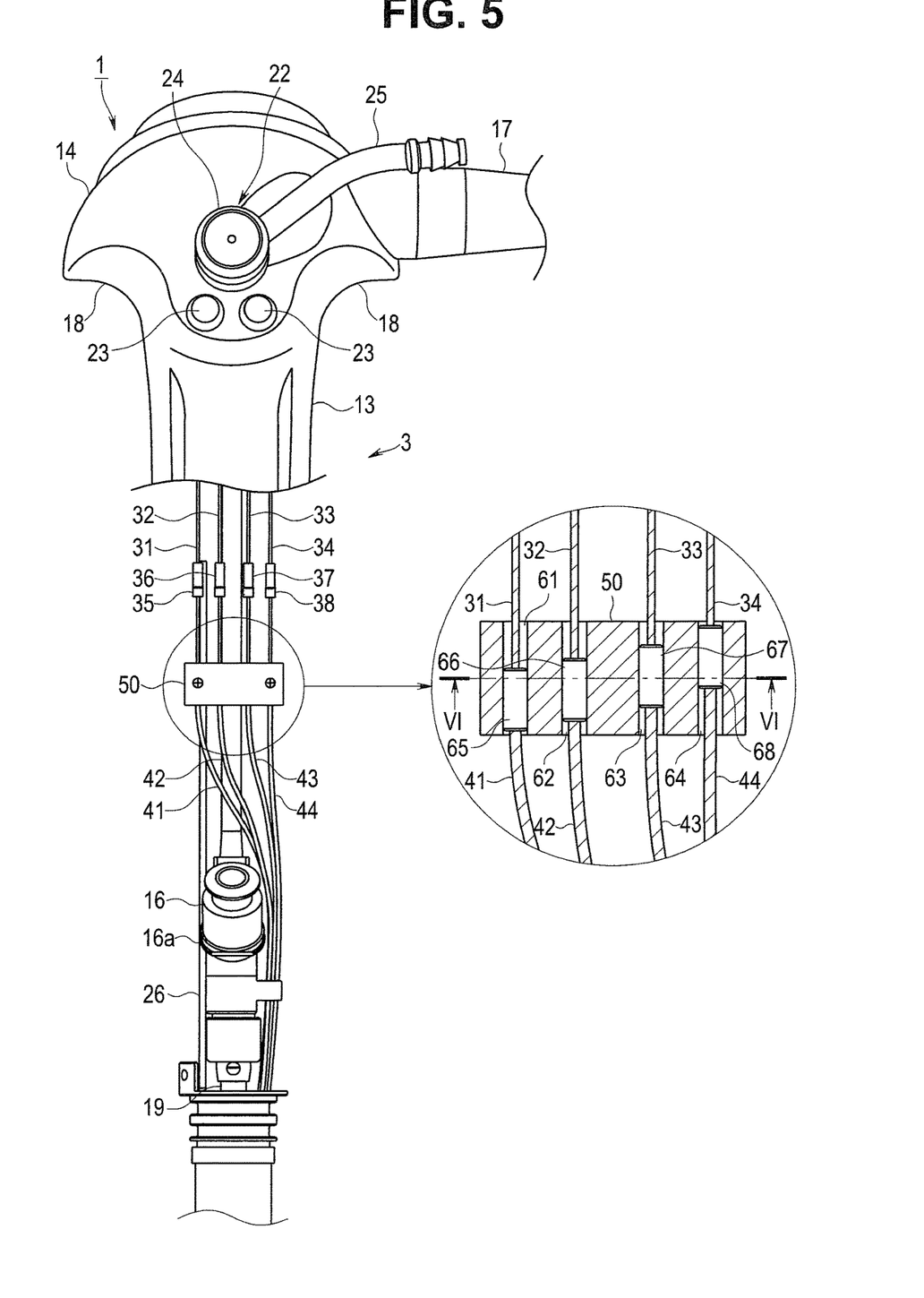
FIG. 5 is a diagram illustrating an internal configuration of an operation portion according to a first modification.
Figure 6:
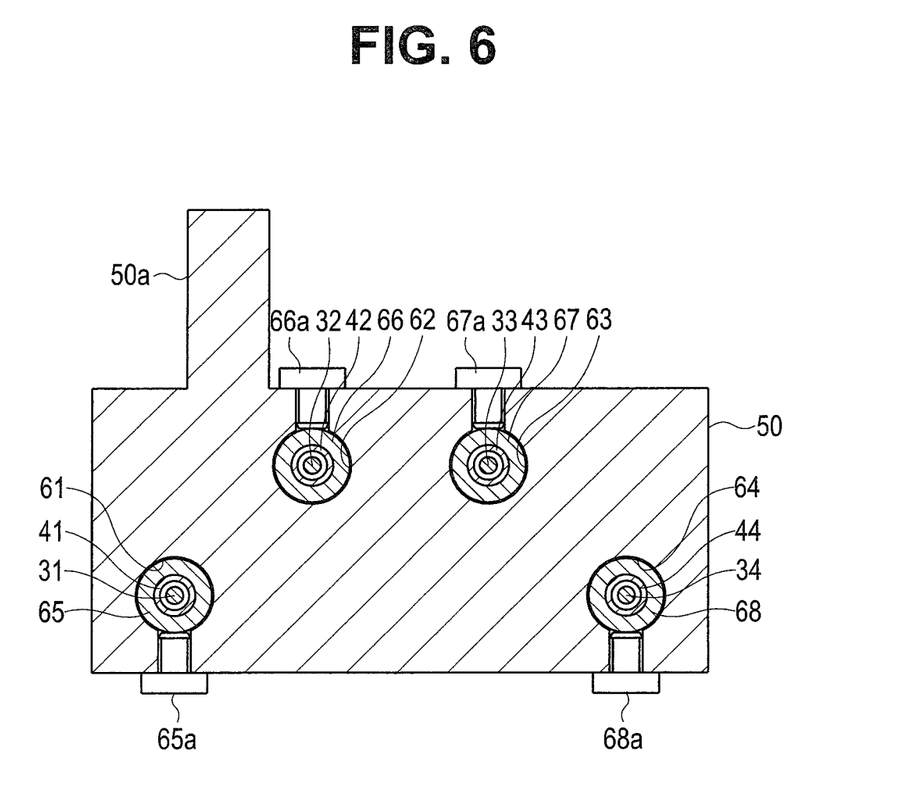
FIG. 6 is a cross-sectional view along a line VI-VI of FIG. 5 according to the first modification.

FIG. 5 is a diagram illustrating an internal configuration of an operation portion according to a first modification and FIG. 6 is a cross-sectional view along a line VI-VI in FIG. 5 according to the first modification.

As shown in FIG. 5 and FIG. 6, the coil receiver 50 of the endoscope 1 according to the present modification is provided with four, first to fourth through holes 61, 62, 63 and 64, which become locking portions. The four, first to fourth coil tubes 41, 42, 43 and 44 of the present modification are provided with four, first to fourth cylindrical anchors 65, 66, 67 and 68, which become locked portions at one end portions, which become respective distal end sides (insertion portion 2 sides). Note that the coil receiver 50 is provided with a convex portion 50a to be fixed to the frame 26 with a fixing member such as a screw (see FIG. 6).

The first to fourth anchors 65, 66, 67 and 68 are configured to be inserted and disposed in first to fourth through holes 61, 62, 63 and 64 of the coil receiver 50 and then respectively fixed from a side circumferential direction to the coil receiver 50 by fixing screws 65a, 66a, 67a and 68a. Note that the coil receiver 50 is provided with screw holes on the side face, which are configured to communicate with the four, first to fourth through holes 61, 62, 63 and 64 and into which the fixing screws 65a, 66a, 67a and 68a are screwed.

By adopting such a configuration, it is possible to adjust fixing positions of the first to fourth anchors 65, 66, 67 and 68 in hole axis directions of the first to fourth through holes 61, 62, 63 and 64 of the coil receiver 50 and more optimally adjust the respective amounts of deflection of the first to fourth coil tubes 41, 42, 43 and 44.

In other words, the coil receiver 50 locks the distal ends of the first to fourth coil tubes 41, 42, 43 and 44 so as to be juxtaposed at different positions along the longitudinal axis in the direction orthogonal to the insertion axis O or the longitudinal axis of the operation portion 3 here, and can thereby optimally adjust the respective amounts of deflection of the first to fourth coil tubes 41, 42, 43 and 44.

As a result, the endoscope 1 of the present modification can better suppress variations in the amounts of traction forces of the first to fourth bending operation wires 31, 32, 33 and 34 for bending the bending portion 7 of the insertion portion 2 and make the bending angle of the bending portion 7 in accordance with the amount of operation of the bending operation lever portion 30 substantially more uniform.

(Second Modification)

Figure 7:
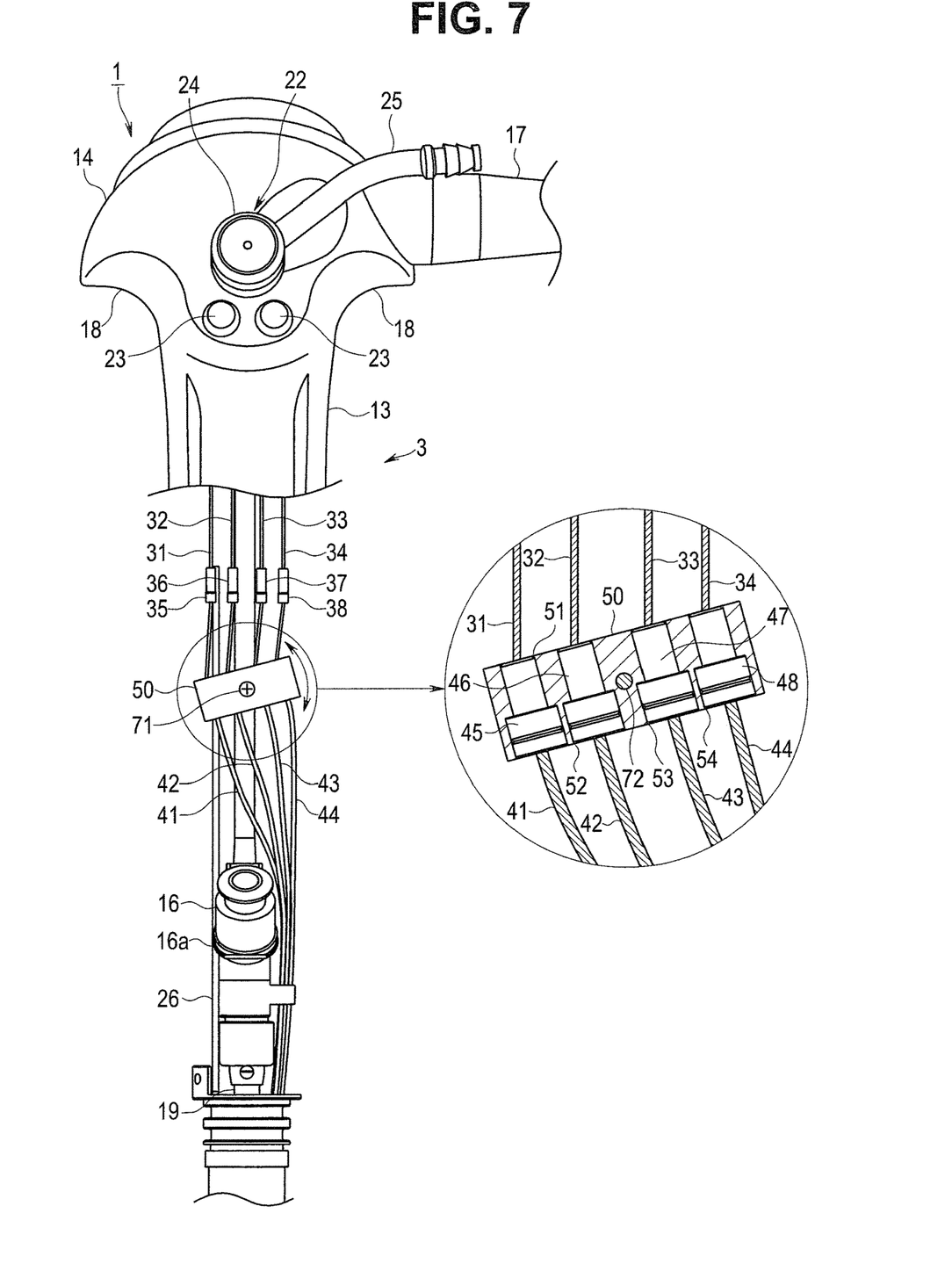
FIG. 7 is a diagram illustrating an internal configuration of an operation portion according to a second modification.

FIG. 7 is a diagram illustrating an internal configuration of an operation portion according to a second modification.

As shown in FIG. 7, the coil receiver 50 of the endoscope 1 in the present modification is rotatably provided around an axis 72 of a fixing screw 71, which becomes a rotation axis, and can be fixed at a desired rotation position by tightening the fixing screw 71. Note that the coil receiver 50 is fixed with the fixing screw 71 being screwed to a protruding portion (not shown) of the frame 26.

The first to fourth locking portions 51, 52, 53 and 54 formed in the coil receiver 50 are formed such that all of heights (depths) of the first to fourth inward flanges 55, 56, 57 and 58 from the top surface side of the coil receiver 50 are the same. Note that the coil receiver 50 here has substantially the same height as the lengths of the first to fourth connection terminals 45, 46, 47 and 48.

By adopting such a configuration, it is possible to rotate the coil receiver 50 to a position at which the respective amounts of deflection of the first to fourth coil tubes 41, 42, 43 and 44 are optimally adjusted and fixed by the fixing screw 71 and more optimally adjust the respective amounts of deflection of the first to fourth coil tubes 41, 42, 43 and 44.

In other words, the coil receiver 50 locks the distal ends of the first to fourth coil tubes 41, 42, 43 and 44 so as to be juxtaposed at different positions along the longitudinal axis in the direction orthogonal to the insertion axis O or the longitudinal axis of the operation portion 3 here, and thereby optimally adjusts the respective amounts of deflection of the first to fourth coil tubes 41, 42, 43 and 44.

As a result, the endoscope 1 of the present modification can also suppress variations in the amounts of traction forces of the first to fourth bending operation wires 31, 32, 33 and 34 for bending the bending portion 7 of the insertion portion 2 and make the bending angle of the bending portion 7 in accordance with the amount of operation of the bending operation lever portion 30 substantially uniform. Note that the axis 72 of the fixing screw 71, which becomes the rotation axis, need not be the center of the coil receiver 50, and the rotation axis can be located anywhere.

(Third Modification)

Figure 8:
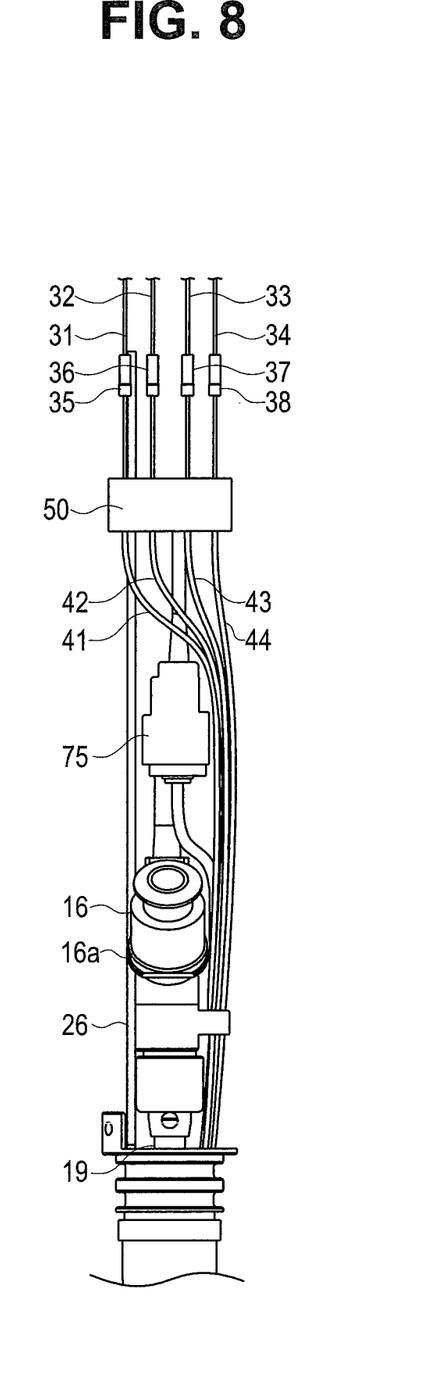
FIG. 8 is a diagram illustrating an internal configuration of an operation portion according to a third modification.

FIG. 8 is a diagram illustrating an internal configuration of an operation portion according to a third modification.

As shown in FIG. 8, in the case of a hybrid scope where the endoscope 1 is provided with an image pickup unit 75, which is an internal component provided with a CCD or CMOS in the operation portion 3, this image pickup unit 75 constitutes an obstacle.

Therefore, even when the first to fourth coil tubes 41, 42, 43 and 44 are disposed so as to avoid the image pickup unit 75, which becomes an obstacle, differences in the amount of deflection can be suppressed by the configuration of the coil receiver 50 in the aforementioned embodiment or modification.

(Fourth Modification)

Figure 9:
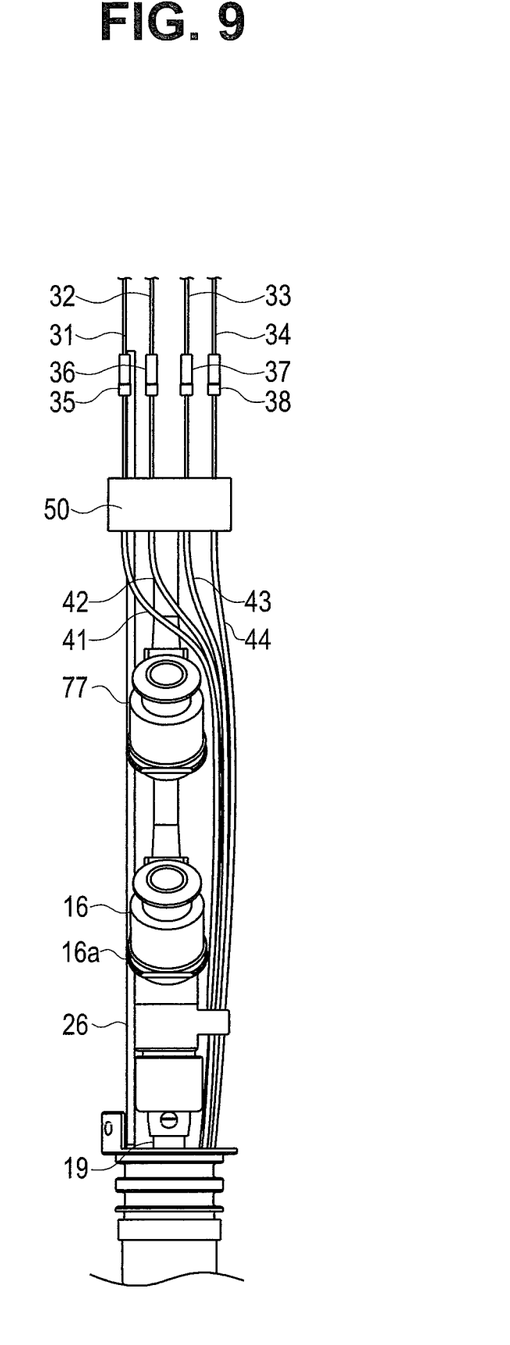
FIG. 9 is a diagram illustrating an internal configuration of an operation portion according to a fourth modification.

FIG. 9 is a diagram illustrating an internal configuration of an operation portion according to a fourth modification.

As shown in FIG. 9, when the endoscope 1 is provided with a balloon water injection port 77, which is an internal component, for injecting water into a balloon in the operation portion 3, this balloon water injection port 77 constitutes an obstacle.

Therefore, even when the first to fourth coil tubes 41, 42, 43 and 44 are disposed so as to avoid the balloon water injection port 77, which may become an obstacle, differences in the amount of deflection can be suppressed by the configuration of the coil receiver 50 in the aforementioned embodiment or modification.

Note that as an internal component in addition to the above components in the operation portion 3, an air/water feeding conduit port, a switch or the like (not shown) may become an obstacle, but even when the first to fourth coil tubes 41, 42, 43 and 44 are disposed so as to avoid these obstacles, differences in the amount of deflection can be suppressed by the configuration of the coil receiver 50 in the aforementioned embodiment or modification.

(Fifth Modification)

Figure 10:
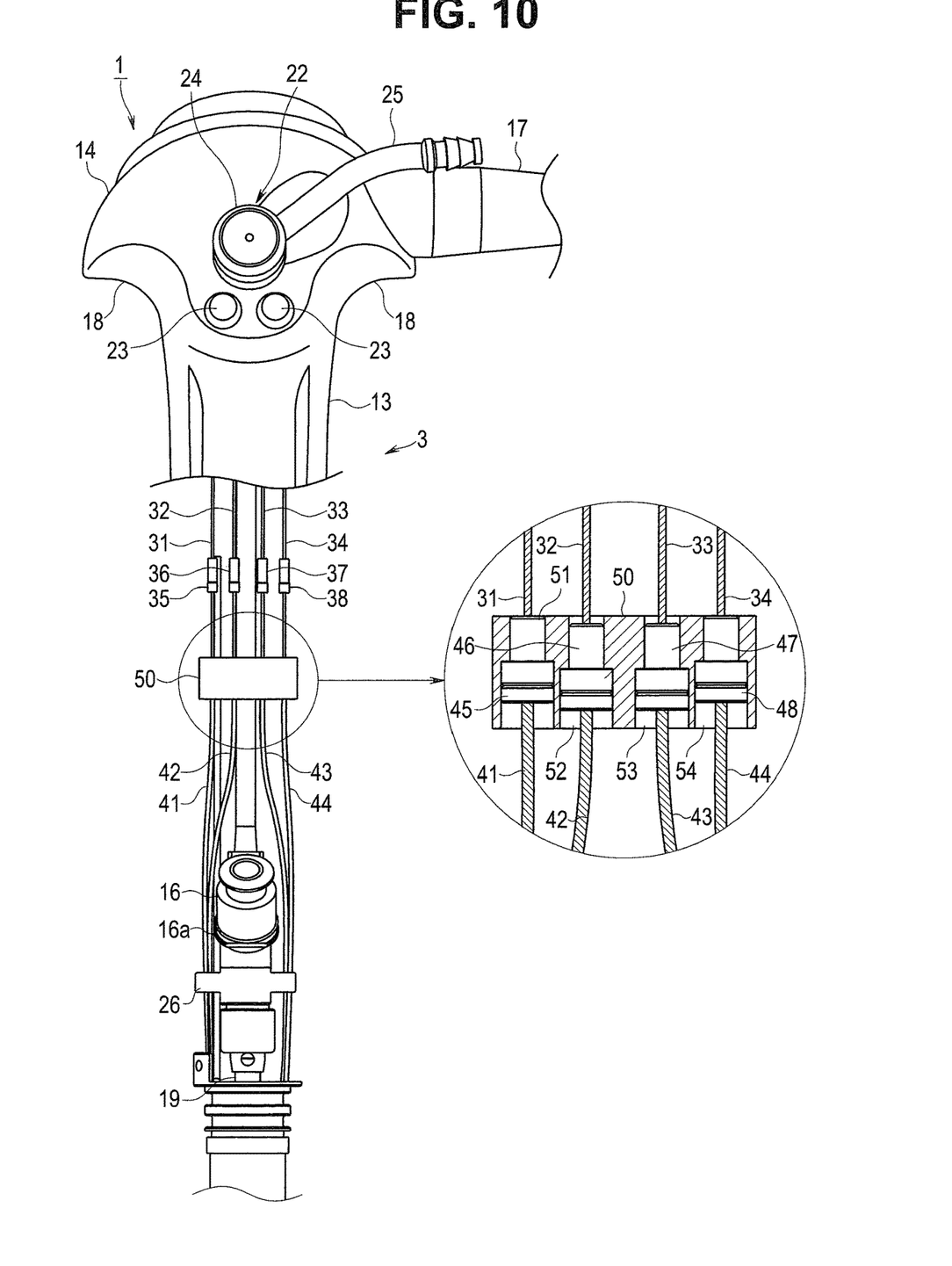
FIG. 10 is a diagram illustrating an internal configuration of an operation portion according to a fifth modification.

FIG. 10 is a diagram illustrating an internal configuration of an operation portion according to a fifth modification.

Configurations have been described so far in which the first to fourth coil tubes 41, 42, 43 and 44 are inserted so as to avoid only one side of the conduit branch portion 16a or the like connected to the treatment instrument insertion port 16, which is an obstacle, whereas as shown in FIG. 10, the coil tubes may be divided into a group of the first and second coil tubes 41 and 42 and a group of the third and fourth coil tubes 43 and 44 so that the coil tubes may be inserted so as to avoid both sides of the obstacle.

In such a case, the first and fourth inward flanges 55 and 58 are formed deeper and the second and third inward flanges 56 and 57 are formed shallower in the first to fourth locking portions 51, 52, 53 and 54 of the coil receiver 50.

In this way, the respective depths of the first to fourth inward flanges 55, 56, 57 and 58 of the first to fourth locking portions 51, 52, 53 and 54 formed in the coil receiver 50 may be set as appropriate according to the configuration in which the first to fourth coil tubes 41, 42, 43 and 44 are inserted so as to avoid the obstacles.

Note that although the bending operation lever portion 30 has been illustrated as a joystick-type bending operation member in the aforementioned embodiment and modifications, the present invention is not limited to this, but the present invention is a configuration applicable to the endoscope 1 having a lever-type or knob-type bending operation member.

The present invention described in the above embodiment and modifications is not limited to the aforementioned embodiment and modifications, but in addition, various modifications can be made without departing from the spirit and scope of the present invention in an implementation stage. Furthermore, each of the aforementioned embodiment and modifications includes inventions in various stages and various kinds of invention can be extracted with an appropriate combination of a plurality of disclosed configuration requirements.

For example, when several configuration requirements are deleted from all configuration requirements disclosed in the aforementioned embodiment and modifications, if the mentioned problems can be solved and the advantageous effects can be achieved, the configuration from which the configuration requirements are deleted can be extracted as an invention.

According to the present invention, it is possible to implement an endoscope capable of suppressing variations in amounts of traction forces of a plurality of bending operation wires for bending the bending portion and make the bending angle of the bending portion substantially uniform in accordance with the amount of operation of the bending operation portion.

What is claimed is:

1. An endoscope comprising:
    a bending operation lever provided at an operation portion and configured to bend a bending portion of an insertion portion;
    a plurality of bending operation wires configured to be pulled or relaxed by the bending operation lever;
    a plurality of tubular members provided inside the operation portion, into which the plurality of bending operation wires are inserted respectively, the plurality of tubular members each being disposed in a different deflected state so as to avoid an internal component provided inside the operation portion; and
    a tubular member fixing body provided inside the operation portion, the tubular member fixing body being configured to adjust a corresponding longitudinal position of each end portion of the plurality of tubular members along a longitudinal axis of the operation portion, the tubular member fixing body being rotatably provided in the operation portion and fixed at a rotated position relative to a direction orthogonal to the longitudinal axis to adjust the corresponding longitudinal position of each end portion of the plurality of tubular members.

2. The endoscope according to claim 1, wherein
    the plurality of bending operation wires each have substantially a same length, and
    the plurality of tubular members each have substantially a same length.

3. The endoscope according to claim 1, wherein
    the plurality of tubular members comprise a locked member at each end portion, and
    the tubular member fixing body comprises a locking surface for engaging with a corresponding locked member to lock each end portion at the corresponding longitudinal position.

4. The endoscope according to claim 3, wherein the tubular member fixing body comprises a through hole corresponding to each of the plurality of tubular members, the through hole having a first diameter and a second diameter smaller than the first diameter, the locking surface comprising a transition between the first diameter and the second diameter.

5. The endoscope according to claim 4, wherein the transition being an inward flange extending radially from the first diameter to the second diameter.

6. The endoscope according to claim 1, wherein
    the plurality of tubular members comprise a locked member at each end portion,
    the tubular member fixing body comprises a plurality of through holes into which the plurality of the locked members are respectively inserted and disposed, and
    the endoscope comprises a projection extending into each of the plurality of through holes for engaging with a corresponding locked member to lock each end portion at the corresponding longitudinal position.

7. The endoscope according to claim 6, wherein the projection is configured such that a length of the projection extending into the through hole is variable.

8. The endoscope according to claim 7, wherein the projection is a screw and the tubular member fixing body comprises a mating threaded hole corresponding to the screw.

9. The endoscope according to claim 1, wherein the internal component is one of a treatment instrument insertion port, a balloon water injection port or an image pickup unit.

10. The endoscope according to claim 1, wherein the tubular member fixing body comprises a rectangular block.

* * * * *